(12) United States Patent
Peter et al.

(10) Patent No.: US 11,541,325 B2
(45) Date of Patent: Jan. 3, 2023

(54) DEVICE FOR EVAPORATING A LIQUID MEDIUM IN A FILLING PRODUCT FILLING SYSTEM

(71) Applicant: KRONES AG, Neutraubling (DE)

(72) Inventors: Michael Peter, Neutraubling (DE); Juergen Soellner, Neutraubling (DE)

(73) Assignee: KRONES AG, Neutraubling (DE)

( * ) Notice: Subject to any disclaimer, the term of this patent is extended or adjusted under 35 U.S.C. 154(b) by 907 days.

(21) Appl. No.: 16/306,878

(22) PCT Filed: Sep. 29, 2017

(86) PCT No.: PCT/EP2017/074772
§ 371 (c)(1),
(2) Date: Dec. 3, 2018

(87) PCT Pub. No.: WO2018/060422
PCT Pub. Date: Apr. 5, 2018

(65) Prior Publication Data
US 2021/0031121 A1    Feb. 4, 2021

(30) Foreign Application Priority Data

Sep. 29, 2016 (DE) .................... 10 2016 118 475.6

(51) Int. Cl.
| | |
|---|---|
| *B01D 1/22* | (2006.01) |
| *B01B 1/00* | (2006.01) |
| *B01D 1/00* | (2006.01) |
| *B01D 1/14* | (2006.01) |
| *A61L 2/20* | (2006.01) |

(52) U.S. Cl.
CPC ................. *B01D 1/22* (2013.01); *B01B 1/00* (2013.01); *B01D 1/0047* (2013.01); *B01D 1/14* (2013.01); *A61L 2/208* (2013.01); *A61L 2202/11* (2013.01)

(58) Field of Classification Search
CPC ....... A61L 2/208; A61L 2202/11; B01D 1/22; B01D 1/14; B01D 1/0047; B01B 1/00
See application file for complete search history.

(56) References Cited

U.S. PATENT DOCUMENTS 2,614,973 A * 10/1952 Burrows .................. B01D 3/08
                                                             202/205
2,955,990 A    10/1960 Smith
(Continued)

FOREIGN PATENT DOCUMENTS

| CN | 101808671 | 8/2010 |
| CN | 102327629 | 1/2012 |

(Continued)

OTHER PUBLICATIONS

Office Action, Chinese Application No. 201780049530.7, dated Jun. 18, 2020, 8 pages.
(Continued)

*Primary Examiner* — Sean E Conley
(74) *Attorney, Agent, or Firm* — Haynes and Boone, LLP

(57) ABSTRACT

A device for evaporating a fluid medium in a filling product filling plant includes an inclined evaporator surface, a medium supply line for applying the fluid medium that is to be evaporated to the evaporator surface, and grooves in the evaporator surface for conducting the fluid medium. The grooves along the evaporator surface have a non-linear design.

16 Claims, 4 Drawing Sheets

(56) References Cited

U.S. PATENT DOCUMENTS

| | | | |
|---|---|---|---|
| 5,112,442 | A | 5/1992 | Goodson |
| 2002/0064487 | A1 | 5/2002 | Sederquist et al. |
| 2004/0050503 | A1* | 3/2004 | Vallejo-Martinez ..... B01D 1/22 159/22 |

FOREIGN PATENT DOCUMENTS

| | | |
|---|---|---|
| CN | 104582809 | 4/2015 |
| DE | 3540161 | 5/1987 |
| DE | 102005023956 | 11/2006 |
| EP | 2407181 | 1/2012 |
| EP | 2604294 | 6/2013 |
| GB | 880990 | 10/1961 |
| GB | 987121 | 3/1965 |
| JP | 1997-294805 A | 11/1997 |
| JP | 2005/065882 | 3/2005 |
| JP | 2005-65882 A | 3/2005 |
| WO | WO 2006/125417 | 11/2006 |
| WO | WO 2014/202393 | 12/2014 |

OTHER PUBLICATIONS

Japanese Office Action dated Sep. 28, 2021 from corresponding Japanese application No. 2018-563608, 5 pages.
International Search Report and Written Opinion issued in International Patent Application No. PCT/EP2017/074772 dated Apr. 10, 2018.

\* cited by examiner

DEVICE FOR EVAPORATING A LIQUID MEDIUM IN A FILLING PRODUCT FILLING SYSTEM

CROSS REFERENCE TO RELATED APPLICATIONS

This application is a national stage of International Application No. PCT/EP2017/074772, filed Sep. 29, 2017, which claims priority from German Patent Application No. 10 2016 118 475.6 filed on Sep. 29, 2016 in the German Patent and Trademark Office, the disclosures of which are incorporated herein by reference in their entirety.

BACKGROUND

Technical Field

The present invention relates to a device for evaporating a fluid medium in a filling product filling plant, for example for evaporating a disinfection medium in a beverage filling plant in order to provide a disinfecting gas for disinfecting areas of the beverage filling plant that come into contact with the filling product. The present device serves, for example, to evaporate hydrogen peroxide for use in a disinfection process in a beverage filling plant.

Related Art

Various types and forms of evaporators are known for evaporating fluid media. These can for example also be used in beverage filling plants to provide gaseous hydrogen peroxide for the disinfection of plant components that come into contact with the product. The evaporators usually have a heated evaporator surface, onto which is sprayed the medium, which is still fluid and is to be evaporated. The fluid medium is then evaporated on the evaporator surface. The evaporator surface is heated, for example by means of hot steam or by means of electrical heating rods, in order to provide the evaporator surface with the desired temperature, which is above the boiling temperature of the fluid medium that is to be evaporated.

From JP 2005 065 882 A2, for example, an evaporator is known for evaporating an aqueous hydrogen peroxide solution which is sprayed onto an inclined evaporator surface of the evaporator, in order to enable evaporation of the hydrogen peroxide solution. The evaporator surface is disposed in an evaporator chamber which is defined by a box-shaped housing which closes the evaporator surface off from the surroundings.

SUMMARY

A device for evaporating a fluid medium which enables a high level of evaporation performance together with a reliable design of the device is described according to various embodiments.

Accordingly, a device for evaporating a fluid medium in a filling product filling plant is proposed, that includes an inclined evaporator surface, a medium supply line for applying the fluid medium that is to be evaporated to the evaporator surface, and grooves in the evaporator surface for conducting the fluid medium. The grooves along the evaporator surface have a non-linear design.

Due to the fact that the grooves which are provided in the evaporator surface for conducting the fluid medium that is to be evaporated have a non-linear design, the fluid medium that is to be evaporated can flow more slowly on the evaporator surface along these grooves, so that a uniform distribution of the fluid medium that is to be evaporated can be provided on the evaporator surface. Accordingly, the evaporator surface can be evenly impinged, over the entire evaporator surface, with the fluid medium that is to be evaporated. Hence the overall evaporation performance can be increased as a result of the larger active evaporator surface.

Furthermore, due to the design of the grooves it is unnecessary to use spray nozzles to apply the fluid medium that is to be evaporated to the evaporator surface. Instead, the medium can simply be applied to the evaporator surface via the medium supply line, and evenly distributed by means of the grooves. The absence of spray nozzles means that no spray nozzle blockage can occur, and in consequence a particularly reliable and low-maintenance device can be proposed.

A "non-linear design" of the grooves is to be understood in particular as meaning that the grooves in the applicable evaporator surface do not extend in a straight line over their entire length. Instead, they undergo a change in direction. This can be achieved, for example, by grooves with curves, spiral grooves, zigzag grooves with abrupt changes in direction, and other groove shapes which do not extend in a straight line over the applicable evaporator surface. The grooves can in particular extend along the evaporator surface in a spiral and/or curved and/or bent form.

By means of the design of the shape of the grooves, it can thus be achieved that the fluid medium that is to be evaporated is distributed on the evaporator surface in a guided manner, so that a largely complete wetting of the evaporator surface with the medium that is to be evaporated is ensured, and a high level of evaporation performance is thereby achieved.

A device for evaporating a fluid medium in a filling product filling plant is proposed according to various embodiments, including an inclined evaporator surface and a medium supply line for supplying the fluid medium that is to be evaporated to the evaporator surface, wherein the evaporator surface is accommodated in an evaporator housing. The contour of the inner wall of the evaporator housing, at least in the region of the inclined evaporator surface, substantially follows the contour of the evaporator surface.

Thus the evaporator surface and the evaporator housing together form an evaporator chamber, in which the volume in which the evaporation takes place is defined by the gap between the evaporator surface and the inner surface of the evaporator housing. Due to the fact that the surfaces run parallel to each other, a channel-shaped structure with a substantially constant spacing is formed. Thus at least in the regions in which the evaporator housing is opposite the evaporator surface and follows its contour, the cross-section of the evaporator chamber is substantially annular in form.

In this manner the volume of the evaporator chamber can be controlled, i.e. kept low enough for the design of the evaporator chamber, and hence the volume of the evaporator chamber, to remain small. This is particularly important with regard to the provisions of the Pressure Equipment Directive 97/23/EC, since pressure vessels are not subject to a final assessment if the pressure/volume product, i.e. the product of the volume of the pressure chamber and the pressure rating of the vessel, is lower than 50. If the volume of the evaporator chamber can be kept low, it is possible thereby to provide a low-maintenance evaporator which is not subject to a final assessment. This is advantageous for reasons of both cost and efficiency of the plant.

The evaporator surface is generally provided by a cone-shaped, or pyramid-shaped, or conoid, or in another manner convex evaporator body. The evaporator body can in particular also be designed as a truncated cone, on whose upper side the fluid medium that is to be evaporated, which flows from the medium supply line, is distributed to the individual grooves and onto the evaporator surface as a whole.

If the inner contour of the evaporator housing follows that of the evaporator surface, only an annular gap, or a gap in the shape of the surface of a cone, is formed between the evaporator surface and the inner surface of the evaporator housing. Along this gap the carrier gas, i.e. the carrier air, can flow across the evaporator surface. Even at higher pressures, which can occur due to the evaporation of the fluid medium, the pressure/volume product can continue to be controlled such that the limit values specified in the Pressure Equipment Directive are not exceeded within the evaporator, and accordingly an efficient and low-maintenance device can be provided.

In some embodiments, the upper region of the evaporator surface is adjoined in an upwards direction by a medium distribution device, which generally has a dome-shaped design. In certain embodiments, the medium distribution device has a dome, upon which the fluid medium is applied by the medium supply line. In a further development, a gutter for accommodating fluid medium is disposed between the dome and the evaporator surface, and generally the grooves which extend along the evaporator surface are in fluid communication with the gutter.

If the evaporator body is in the shape of a cone or a truncated cone, the grooves that extend along the evaporator surface are typically spiral in form, as viewed along the axis of the cone.

A medium supply line is generally provided, which enables the fluid medium that is to be evaporated to be supplied to the inclined evaporator surface, in each case to the uppermost region of the inclined evaporator surface. Due to the grooves, the supply of medium can take place without the use of spray nozzles, since the distribution over the evaporator surface of the fluid medium that is to be evaporated is carried out by the non-linear grooves.

Due to the fact that spraying of the medium onto the evaporator surface can be dispensed with, it is also possible to avoid disruptions caused by blockage of spray nozzles, such as are known in conventional evaporators. Instead, via a medium supply line, for example in the form of a tube with a specified cross-section, the fluid medium that is to be evaporated can be applied to the uppermost point, or the uppermost region, of the evaporator surface, without any variation in the cross-section of the medium supply tube.

The cross-section of the tube for supplying medium is generally chosen such that fluid medium that is to be evaporated can be supplied constantly in a quantity which can also be evaporated directly by the device. In other words, the medium that is supplied is evaporated immediately, and the medium supply line can be operated continuously.

A carrier gas is typically supplied to the evaporator chamber via a carrier gas supply line, and subsequently discharged from the evaporator chamber via a gas outlet for discharging the carrier gas that is enriched with the evaporated medium.

In several embodiments, the carrier gas supply line is configured such that it directs the carrier gas onto the evaporator surface with an impulse, in order in this manner further to promote efficient evaporation. By means of the flow of carrier gas around or over the evaporator surface, the evaporated fluid medium together with the carrier gas can be efficiently transported away.

The carrier gas supply can generally be blown into the evaporator chamber via a nozzle, such that a turbulent, swirling flow is created along the evaporator surface, in order that the evaporated medium can be efficiently transported away.

In various embodiments, the carrier gas supply line can include a carrier gas channel, which is arranged around the periphery of a cone-shaped and/or pyramid-shaped, and/or conoid evaporator surface, and which outputs the carrier gas onto the evaporator surface via carrier gas outlets. By this means an even flow of the carrier gas across the evaporator surface can be achieved, with the result that efficient utilization of the entire evaporator surface is achieved.

In an embodiment of the device for evaporating, the blowing in of the carrier gas, i.e. the air which is to be enriched with the evaporated fluid medium, is performed via a plurality of supply apertures or a supply slot, in order thereby to achieve a substantially uniform impingement of the evaporator surface with the carrier gas. In this manner, the efficiency of the evaporation can be increased, and at the same time it can be ensured that the evaporated fluid medium is transported away reliably and evenly.

The gas flow along the evaporator surface is typically designed to be turbulent, in order to aid the transporting away of the evaporation products and/or the mixing of the evaporated fluid medium into the carrier gas. For reasons of energy efficiency, the flow can however also be designed to be laminar, in order to reduce the resistance that is present inside the evaporation chamber.

In certain embodiments, a heating device for the evaporator surface is provided, which is configured to operate with a heating medium that has a boiling temperature above the working temperature of the evaporator surface. By means of this design of the heating device, heating can take place without the device being subject to further restrictions arising from the Pressure Equipment Directive. As an efficient heating medium, it is for example possible to use a thermal oil, which can be supplied to the evaporator body at a low pressure.

BRIEF DESCRIPTION OF THE FIGURES

Further embodiments of the invention are more fully explained by the description below of the figures.

DETAILED DESCRIPTION

Examples of embodiments are described below with the aid of the figures. In the figures, elements which are identical or similar, or have identical effects, are designated with identical reference signs. In order to avoid redundancy, repeated description of these elements is in part dispensed with in the description below.

Figure 1:
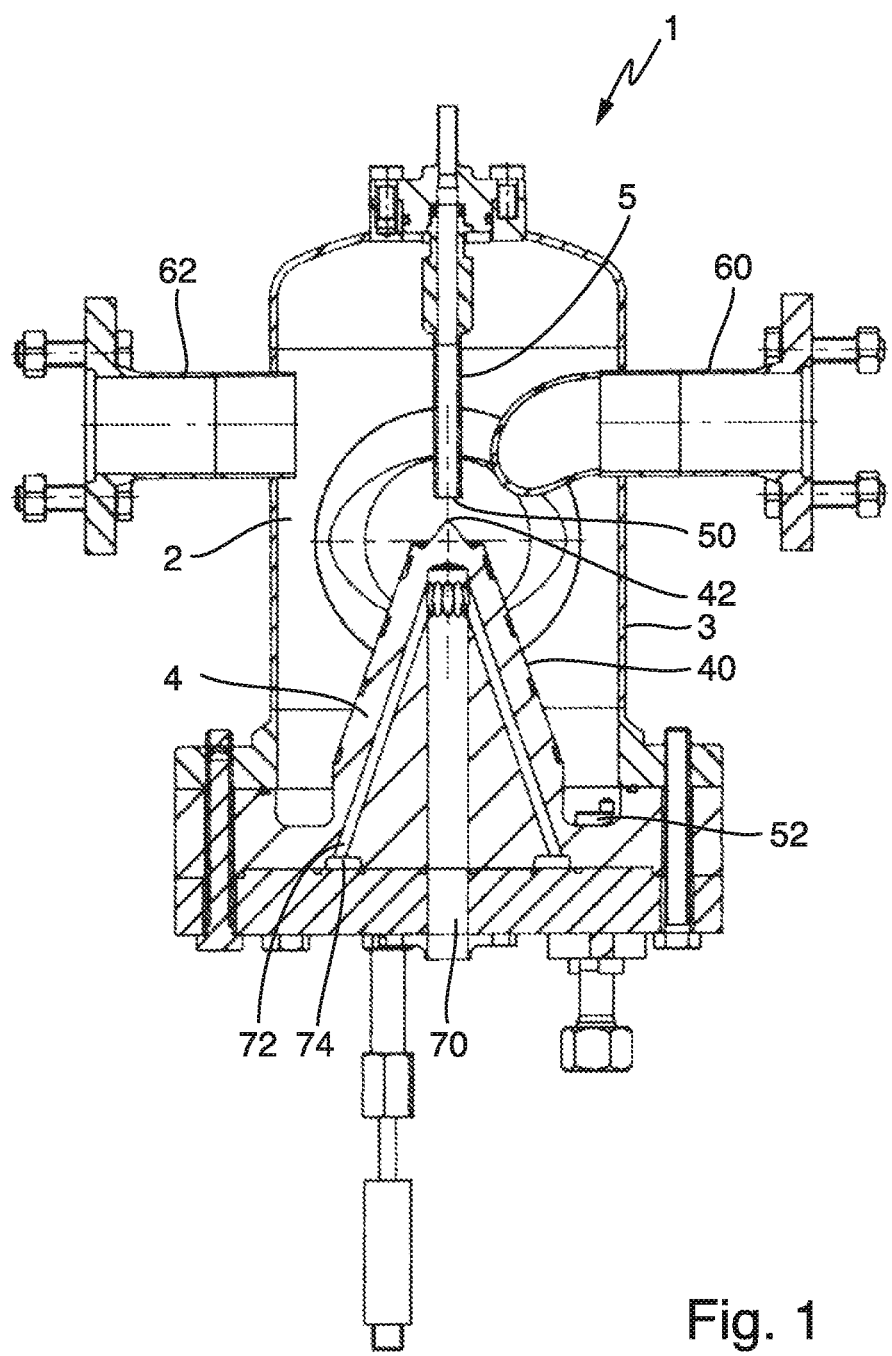
FIG. 1 is a schematic sectional representation through a device for evaporating a fluid medium in the form of an aqueous $H_2O_2$ solution.
Figure 2:
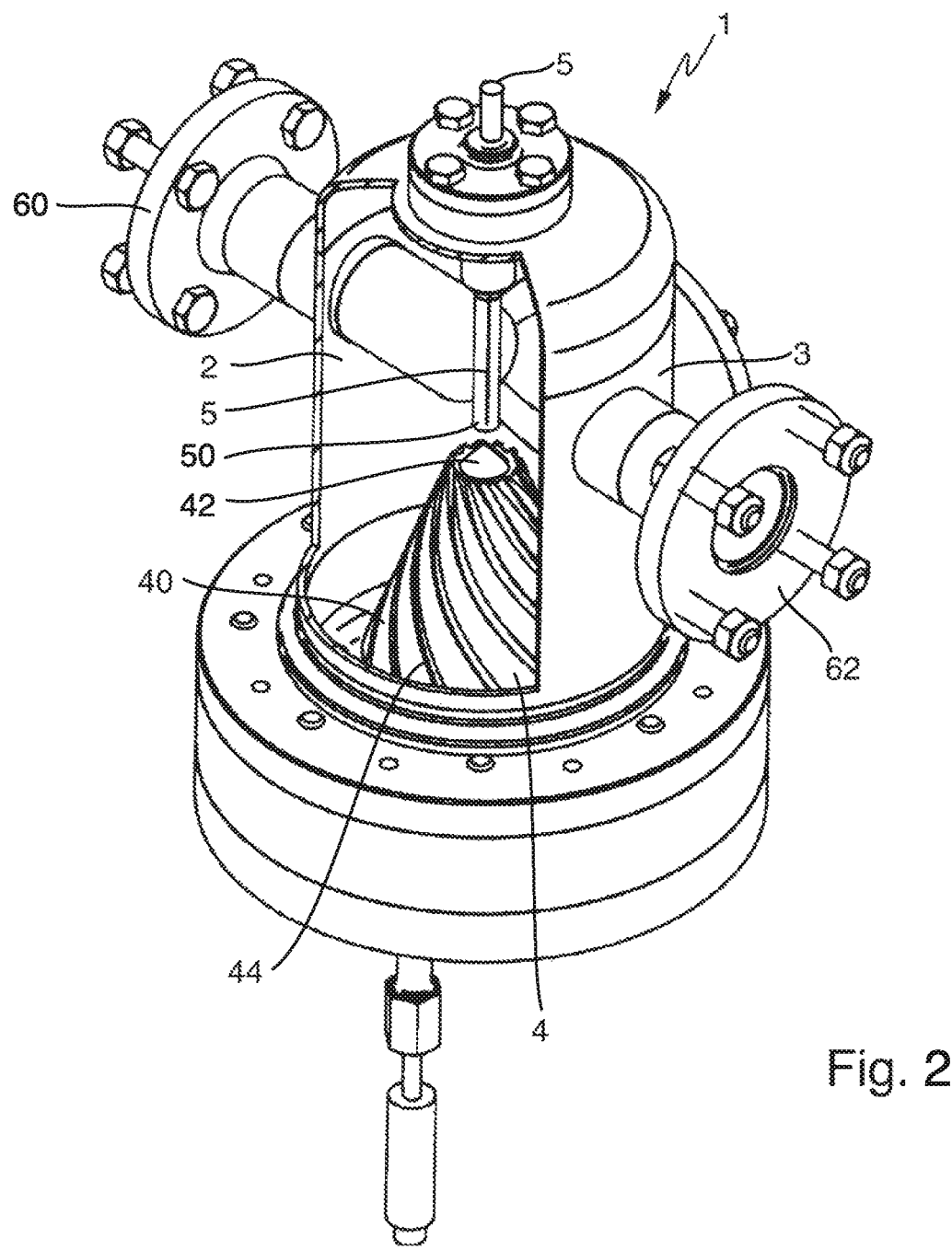
FIG. 2 is a partially sectional perspective representation of the device from FIG. 1.
Figure 3:
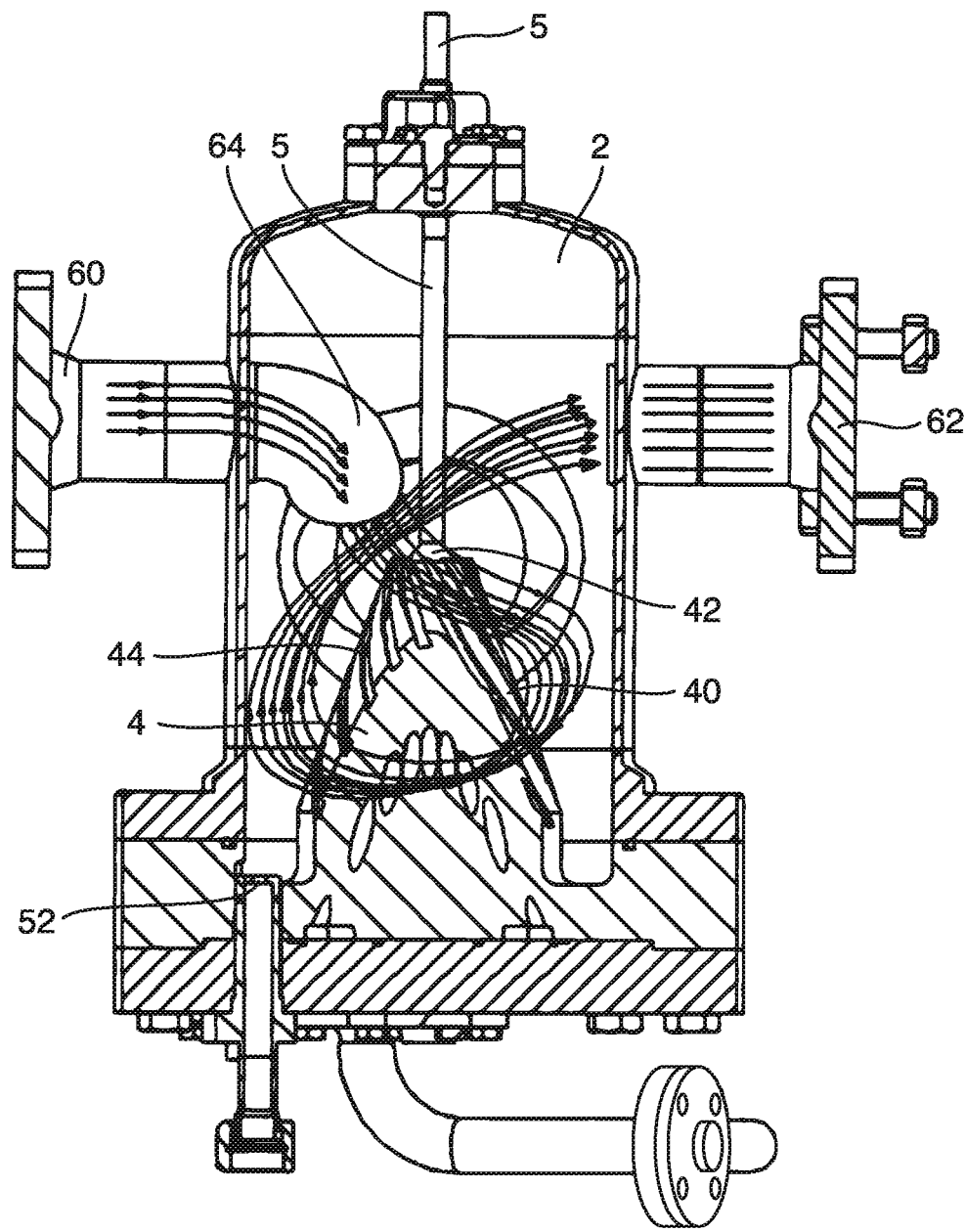
FIG. 3 is a schematic sectional representation of the device from FIGS. 1 and 2, in which the airflow that passes through the evaporator chamber is indicated schematically.

FIGS. 1 to 3 show schematic representations of a device 1 for evaporating a fluid medium. As the fluid medium, for example an aqueous 35% solution of $H_2O_2$ is evaporated in the device 1, and used to enrich a carrier gas, for example air. After being enriched with the evaporated fluid medium, the carrier gas is for example subsequently used in a disinfection process in a filling product filling plant, in order for example to carry out a scheduled disinfection of the plant or to restore it to a hygienically acceptable state following conversion or downtime, so that the next filling with a filling product, for example a beverage or another foodstuff, can take place in a hygienically acceptable manner.

The device 1 for evaporating the fluid medium includes an evaporator chamber 2, which is defined by an evaporator housing 3. In the evaporator housing 3, and thus in the evaporator chamber 2, an evaporator body 4 is provided, which forms an evaporator surface 40. The evaporator surface 40 has an inclined orientation, so that the fluid medium that is applied to it flows basically downwards.

Via a medium supply line 5, the fluid medium that is to be evaporated is applied to the evaporator surface 40 of the evaporator body 4, and accordingly evaporated on the evaporator surface 40, so that the evaporated medium enters the evaporator chamber 2.

In order to enable the evaporated medium, which has been evaporated on the evaporator surface 40 and is present in the evaporator chamber 2, to be transported away and subsequently used in a filling product filling plant, for example for disinfection, a carrier gas is introduced into the evaporator chamber 2 via a carrier gas supply line 60. The carrier gas, together with the medium that was evaporated on the evaporator surface 40, is then discharged via a gas outlet 62. The gas outlet 62 thereby serves to transfer the evaporated medium, together with the carrier gas, to a subsequent treatment step. The carrier gas can be for example air.

In the example embodiment that is shown, the evaporator body 4 has a substantially conical design. Thus the evaporator surface 40 is designed in the form of the surface of a cone. The cone-shaped design of the evaporator body 4 enables a relatively large evaporator surface 40 to be provided on a relatively small base area, and thus enables the provision of a device 1 that is without indentations and easy to clean.

The fluid medium that is supplied via the medium supply line 5, which in the example embodiment that is shown is designed in the form of a supply tube through which the $H_2O_2$ solution is applied to the evaporator surface 40, is enabled to flow evenly onto the evaporator surface 40 by means of a dome 42, which is provided in the upper region of the evaporator body 4 and which distributes the medium which flows from the medium supply line 5 uniformly around the circumference of the evaporator surface 40.

For this purpose, a gutter can be disposed between the dome 42 and the evaporator surface 40. The gutter holds back the fluid medium until it overflows, which leads to a uniform distribution of the fluid medium on the evaporator surface 40, and in particular a uniform distribution around the circumference.

In addition, grooves 44 are provided in the evaporator surface 40. Along these, the medium that is to be evaporated is conducted, and can thereby be distributed over the evaporator surface 40.

The grooves 44 that are disposed in the evaporator surface 40 of the evaporator body 4 are arranged on the evaporator surface in a non-linear manner, i.e. curved or bent, as can be seen particularly well, for example, in FIG. 2. The grooves 44 are generally in fluid communication with the gutter, and in a further development they issue from the gutter.

In the particular embodiment that is shown in FIGS. 1 to 3, the grooves 44 are arranged in spiral-shaped sections on the evaporator surface 40. The non-linear, and particularly the spiral arrangement of the grooves 44, enables efficient transport of the fluid and not yet evaporated medium over the entire evaporator surface 40. At the same time, the spiral design prevents the fluid and not yet evaporated medium from flowing downwards at once and collecting in the lower region only. Instead, it can be achieved by the non-linear, i.e. spiral, design of the grooves 44 that the fluid and not yet evaporated medium, which is however still to be evaporated, flows more slowly and spreads itself evenly over the evaporator surface 40. Thus it is possible to achieve a particularly efficient evaporation of the fluid medium that is to be evaporated, since all surface areas of the evaporator surface 40 can be uniformly and continuously impinged with the fluid medium.

In some embodiments, the grooves 44 extend from the uppermost region of the evaporator surface 40 to its lowest region, so that a uniform distribution of the fluid medium over the entire evaporator surface 40 can be achieved.

In the example embodiment that is shown, the medium supply line 5 is designed in the form of a tube, which has no taper or nozzle at its outlet end 50. In other words, the fluid medium that is to be evaporated flows directly onto the dome 42 of the evaporator body 4, and it is only by means of the dome 42 that it is distributed on the evaporator surface 40. Thus the medium supply line 5 is not equipped with a nozzle for spraying the medium that is to be evaporated. Hence it is possible to achieve reliable operation and a reduction of the maintenance that is required of the medium supply line 5 within the device 1, due to the fact that no clogging or blockage of nozzles for supplying the medium that is to be evaporated occurs, and no such nozzles need to be readjusted.

The evaporator body 4 has a heating circuit, which provides a heating medium supply line 70 in the form of a central bore within the cone-shaped evaporator body 4. A heating medium return line 72 is provided in the form of a plurality of bores in the evaporator body 4, which extend radially from an upper region of the heating medium supply line 70, parallel to the evaporator surface 40. Thus the heating medium can be conveyed upwards via the heating medium supply line 70 through the center of the evaporator body 4, and then be conveyed back via the heating medium return line 72 along the evaporator surface 40 within the evaporator body 4, so that heat can be evenly and efficiently transferred to the evaporator surface 40 within the evaporator body 4. At the lower end of the evaporator body 4, the heating medium return line 72 in the form of bores extending parallel to the evaporator surface 40 flows into a return channel 74, by means of which the heating medium can then be conveyed back to an external heat exchanger.

The heating medium that is used generally has a boiling temperature that is above the working temperature of the device 1, i.e. above the desired working temperature of the evaporator surface 40. In the embodiment that is shown, a thermal oil whose boiling temperature is considerably above the working temperature of the evaporator surface 40 is typically used. In this manner the heating circuit with the heating medium supply line 70 and the heating medium return line 72, along with the return channel 74, can be operated at a low pressure, and the occurrence of pressure peaks due to evaporation of the heating medium inside the heating circuit can be avoided. In this manner a heating of the evaporator surface 40 can be provided particularly safely.

As alternatives to the heating of the evaporator body 4 in the manner described above, via a thermal oil or another heat-carrying medium with a boiling temperature above the working temperature of the evaporator surface 40, the evaporator body 4 and in particular the evaporator surface 40 can also be heated with electrical heating rods or in another known manner, in order simultaneously to provide a high level of operational safety and on the other hand achieve a reliable and even heating of the evaporator surface 40.

The portion of the fluid medium which is supplied via the medium supply line 5, and in particular the outlet end 50 of the medium supply line 5, but which is not evaporated on the evaporator surface 40, can be drained out of the evaporator chamber 2, periodically or according to need, via a medium outlet 52 which is disposed in the lower region of the evaporator chamber 2, and can thereby be removed.

As can be seen for example from the representation in FIG. 3, the carrier gas is blown via the carrier gas supply line 60 into the evaporator chamber 2. The carrier gas supply line 60 has a deflection region 64, by means of which the carrier gas can be blown directly onto the evaporator surface 40 of the evaporator body 4, for example as indicated in FIG. 3 by the schematically represented arrows inside the evaporator chamber 2. In this manner it can be achieved that the flow of carrier gas which is supplied via the carrier gas supply line 60 impinges on the evaporator surface 40 in a swirling and turbulent flow, and in this manner enables efficient transporting away of the evaporated fluid medium.

The creation of the turbulent flow is further assisted by the grooves 44 which are provided in the evaporator surface 40 of the evaporator body 4, so that, due to the multilayered and diverse swirling motion, a particularly efficient transportation away of the products of evaporation is also achieved at the grooves 44.

Figure 4:
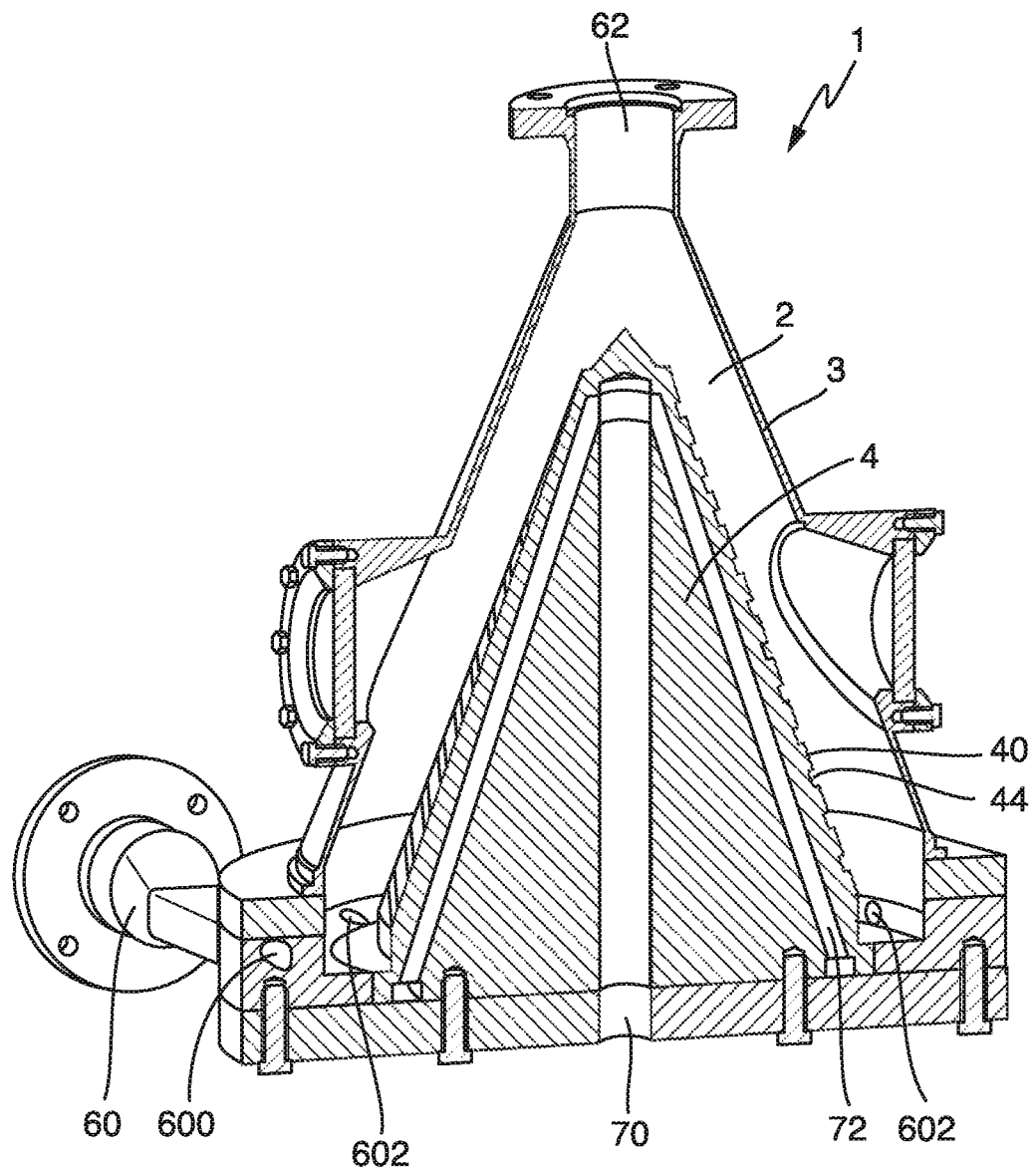
FIG. 4 is a schematic partially sectional perspective representation of a device for evaporating a fluid medium in a further embodiment.

In an alternative embodiment, which is shown in a schematic partially sectional perspective representation in FIG. 4, the device 1 for evaporating a fluid medium is again provided with an evaporator chamber 2, which is formed by an evaporator housing 3, in which a cone-shaped evaporator body 4 is provided. The design of the evaporator body 4 with its conical form, and thus of the evaporator surface 40 in the shape of the surface of a cone, corresponds substantially to that of the embodiments discussed previously.

In the example embodiment in FIG. 4, however, the evaporator housing 3 is designed such that the contour of the inner surface of the evaporator housing 3 substantially follows the contour of the evaporator surface 40 of the evaporator body 4. Thus the evaporator housing 3 also has a substantially conical design, so that the cavity of the evaporator chamber 2 that is formed between the evaporator surface 40 and the inner surface of the evaporator housing 3 corresponds in its cross-section to an annular channel. The evaporator surface 40 and the inner surface of the evaporator housing 3 thus run substantially parallel to each other.

In this manner it can be achieved that the volume of the evaporator chamber 2, which is defined by the inner wall of the evaporator housing 3 and reduced by the volume displacement of the evaporator body 4, can be controlled such that the evaporator chamber 2 forms only a relatively small volume. Accordingly, and with regard to the provisions of the Pressure Equipment Directive 97/23/EC, the pressure/volume product of the device 1 for evaporating the fluid medium can be kept small enough to exempt the pressure vessel from a final assessment in accordance with the Pressure Equipment Directive.

The "pressure/volume product" or "pressure/contents product" is to be understood as the value resulting from the multiplication of the volume of the pressure chamber and the pressure rating of the vessel. According to the Pressure Equipment Directive, this value must be smaller than 50 bar*l in order for the vessel not to be subject to a final assessment. If, for example, the evaporator chamber 2 has a volume of 8 liters, this value is reached at a working pressure of 6 bar. In this example, a pressure/volume product of 48 bar*l is reached.

Accordingly, by means of the dimensioning of the evaporator body 4 and the geometrical configuration of the evaporator housing 3 that surrounds the evaporator body 4, such that the evaporator chamber 2 has as small a volume as possible, it can be achieved that the evaporator is exempt from a final assessment due to its low pressure/volume product, despite being designed for higher pressures. As a result, the installation and maintenance costs, as well as the expenditure of time, can be reduced.

In the example embodiment shown in FIG. 4, the guidance of the airflow of the carrier gas is achieved by the provision of a carrier gas supply line 60, which blows the carrier gas into a carrier gas channel 600 which extends around the lower circumference of the evaporator body 4, and by the provision around the circumference of the evaporator body 4, which is here designed in the form of a cone, of a plurality of carrier gas outlets 602, which enable the carrier gas to flow into the evaporator chamber 2. Thus the carrier gas, which is supplied via the carrier gas supply line 60, and is distributed via the carrier gas channel 600 around the circumference of the evaporator chamber 2 in its base area, is blown into the evaporator chamber 2 via the carrier gas outlets 602. Thus an even supply of the carrier gas into the evaporator chamber 2 takes place, so that the carrier gas can flow across the evaporator surface 40 of the evaporator body 4, in order then to be output from the gas outlet 62 together with the products of evaporation.

In the example embodiment that is shown, due to the conical tapering of the evaporator chamber 2 there is a reduction in the cross-section of the evaporator chamber 2 towards its top—i.e. towards the gas outlet 62. This results in an increase in the flow speed of the carrier gas within the evaporator chamber 2. This correlates with the temperature distribution on the evaporator surface 40 which is due to the conveying of the flow of heating medium in the heating medium supply line 70 and the heating medium return line 72, such that the evaporator surface 40 is slightly warmer in its upper region than in its lower region. In addition, the extent of the evaporator surface 40 is reduced in its upper region, so that, due to the higher flow speed and the higher temperature, a high level of evaporation performance can nevertheless be maintained.

If such a pressure gradient, and gradient in the flow speed of the carrier gas within the evaporator chamber 2, are not desired, instead of the design of the evaporator housing 3 with an inclination of its inner walls that is identical to the inclination of the evaporator surface 40, an evaporator chamber 2 can be designed in which the evaporator housing 3 widens outwards as it rises in the direction of the tip of the cone of the evaporator body 4, in order to provide a uniform flow cross-section over the entire extent of the evaporator chamber 2.

To the extent applicable, all individual features that are described in the individual example embodiments can be combined with each other and/or exchanged, without departing from the field of the invention.

The invention claimed is:

1. A device for evaporating a fluid medium in a filling product filling system, comprising:
   an inclined evaporator surface, wherein the inclined evaporator surface comprises grooves configured to conduct the fluid medium, and the grooves extend along the inclined evaporator surface in a spiral form;
   a medium supply line configured to apply the fluid medium that is to be evaporated to the inclined evaporator surface; and
   a carrier gas supply line configured to conduct a carrier gas onto the inclined evaporator surface, wherein the carrier gas supply line comprises a carrier gas channel that is arranged around a periphery of the inclined evaporator surface and outputs the carrier gas onto the inclined evaporator surface via carrier gas outlets.

2. The device of claim 1, further comprising an evaporator housing, wherein the inclined evaporator surface is accommodated in the evaporator housing and a contour of an inner wall of the evaporator housing substantially follows a contour of the inclined evaporator surface.

3. The device of claim 1, wherein the inclined evaporator surface is disposed on an evaporator body that is in a shape of a cone.

4. The device of claim 3, wherein the evaporator body comprises a dome in an upper region of the evaporator body.

5. The device of claim 4, wherein the medium supply line is configured to apply the fluid medium onto the dome.

6. A device for evaporating a fluid medium in a filling product filling system, comprising:
   an inclined evaporator surface, wherein the inclined evaporator surface comprises grooves configured to conduct the fluid medium, and the grooves extend along the inclined evaporator surface in a spiral form;
   a medium supply line configured to supply the fluid medium that is to be evaporated to the inclined evaporator surface;
   an evaporator housing configured to accommodate the inclined evaporator surface, wherein a contour of an inner wall of the evaporator housing, at least in a region of the inclined evaporator surface, substantially follows a contour of the inclined evaporator surface; and
   a carrier gas supply line configured to conduct a carrier gas onto the inclined evaporator surface, wherein the carrier gas supply line comprises a carrier gas channel that is arranged around a periphery of the inclined evaporator surface and outputs the carrier gas onto the inclined evaporator surface via carrier gas outlets.

7. The device of claim 6, wherein the inclined evaporator surface is disposed on an evaporator body that is in a shape of a cone.

8. The device of claim 7, wherein the evaporator body comprises a dome in an upper region of the evaporator body.

9. The device of claim 8, wherein the medium supply line is configured to apply the fluid medium onto the dome.

10. The device of claim 8, further comprising a gutter configured to accommodate the fluid medium disposed between the dome and the inclined evaporator surface.

11. The device of claim 10, wherein the grooves are in fluid communication with the gutter.

12. The device of claim 6, further comprising a heating device configured to operate with a heating medium having a boiling temperature above a working temperature of the inclined evaporator surface.

13. The device of claim 6, wherein the medium supply line comprises a tube having a substantially constant cross-section.

14. A device for evaporating a fluid medium in a filling product filling system, comprising:
   an inclined evaporator surface, wherein the inclined evaporator surface is disposed on an evaporator body that is in a shape of a cone, and the evaporator body comprises a dome in an upper region of the evaporator body; and
   a medium supply line configured to apply the fluid medium that is to be evaporated to the inclined evaporator surface,
   wherein the inclined evaporator surface comprises grooves configured to conduct the fluid medium, and the grooves are arranged on the inclined evaporator surface in a non-linear design.

15. The device of claim 14, further comprising a carrier gas supply line configured to conduct a carrier gas onto the inclined evaporator surface.

16. The device of claim 15, wherein the carrier gas supply line comprises a carrier gas channel that is arranged around a periphery of the inclined evaporator surface and outputs the carrier gas onto the inclined evaporator surface via carrier gas outlets.

* * * * *